ǁ US010416133B2

United States Patent
Nakashima et al.

(10) Patent No.: US 10,416,133 B2
(45) Date of Patent: Sep. 17, 2019

(54) CHROMATOGRAPHIC DATA PROCESSING DEVICE, DATA PROCESSING METHOD, AND CHROMATOGRAPHIC ANALYSIS SYSTEM

(71) Applicant: SHIMADZU CORPORATION, Kyoto-shi, Kyoto (JP)

(72) Inventors: Minori Nakashima, Kyoto (JP); Yusuke Osaka, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 406 days.

(21) Appl. No.: 15/352,768

(22) Filed: Nov. 16, 2016

(65) Prior Publication Data

US 2018/0136175 A1    May 17, 2018

(51) Int. Cl.
G01N 30/86    (2006.01)

(52) U.S. Cl.
CPC ..... *G01N 30/8631* (2013.01); *G01N 30/8644* (2013.01); *G01N 30/8658* (2013.01); *G01N 30/8679* (2013.01)

(58) Field of Classification Search
CPC .......... G01N 30/8631; G01N 30/8634; G01N 30/8644; G01N 30/8658; G01N 30/8679; G01N 30/8689
See application file for complete search history.

(56) References Cited

U.S. PATENT DOCUMENTS

2015/0308992 A1    10/2015   Yanagisawa

FOREIGN PATENT DOCUMENTS

| JP | 2006-292641 A | 10/2006 |
|----|---------------|---------|
| JP | 2009-109196 A | 5/2009  |
| WO | 2014/087770 A1 | 6/2014 |

OTHER PUBLICATIONS

Toshinobu Yanagisawa, New Data Processing Method for Photodiode Array Detector, Mar. 2013, Shimadzu Technical Report, Analytical & Measuring Instruments Division, 4 pp. (Year: 2013).*
Communication dated Jun. 20, 2017, issued by the Japanese Patent Office in counterpart application No. 2014-143109.

* cited by examiner

*Primary Examiner* — Toan M Le
(74) *Attorney, Agent, or Firm* — Sughrue Mion, PLLC

(57) ABSTRACT

A chromatographic data processing device, data processing method, and chromatographic analysis system. When chromatographic analysis is performed, the data processing device obtains 3D data for time, wavelength, and strength from the PDA, and finds the assay value for the target component in the liquid sample by processing said data. If the peak top strength of the target component falls outside of the dynamic range, a dilution ratio for the liquid sample is determined by calculating the peak top strength of the target component using the ratio of the strength at the peak top wavelength on the spectrum for each point in time belonging to the peak to the strength of a separate wavelength.

14 Claims, 7 Drawing Sheets

Chromatogram at wavelength λ2

Spectrum at time t

CHROMATOGRAPHIC DATA PROCESSING DEVICE, DATA PROCESSING METHOD, AND CHROMATOGRAPHIC ANALYSIS SYSTEM

TECHNICAL FIELD

This invention relates to a data processing device, data processing method, and chromatographic analysis system for a chromatography instrument such as a liquid chromatograph, gas chromatograph, or the like.

BACKGROUND ART

A chromatography instrument acquires data expressing a chromatogram with time on the X axis and signal strength (output voltage or the like) on the Y axis (hereinafter referred to as chromatogram data) by analyzing a sample. Chromatographic data processing devices detect peaks occurring in a chromatogram of this kind, and identify the substance corresponding to a peak from the location of the peak (retention time) by referring to a pre-set identification table, as well as calculating the concentration and quantity of that substance from the height and area of the peak.

In data processing devices of this kind, there is generally a limit to the size of signals that can be processed, arising from the constraints of the hardware of the signal processing circuit such as the A/D converter, meaning that computations cannot be performed accurately if signals of a size exceeding the upper or lower limit are input.

Furthermore, entirely unrelated to this signal processing limit, the reliability of detection results will differ depending on the level of the signal from the chromatography instrument's detector. For example, in the case of a UV-visible spectrophotometer, photodiode array detector, or the like, which are used as detectors in liquid chromatographs, non-linearity typically becomes more pronounced as the concentration of components in the sample increases, as shown in FIG. 10, which impairs assay accuracy. Accordingly, it is desirable to perform analysis in such a way that the concentration of the target component in the sample is within a designated range (dynamic range).

PRIOR ART LITERATURE

Patent Literature (Patent literature 1) Japanese Unexamined Patent Application Publication 2006-292641

SUMMARY OF THE INVENTION

Problem to be Solved by the Invention

If the concentration range of the target component contained in the sample is already known, preprocessing such as diluting or concentrating the sample by an appropriate factor is performed prior to analysis in order to ensure that the detection strength falls within the dynamic range (see Patent Literature 1). However, if nothing is known about the concentration range, it is necessary to rely on the experience and intuition of the assayer in regards to what dilution ratio or concentration ratio to use for the sample. For this reason, novices with little experience were forced to either perform repeat measurements while gradually changing the dilution ratio or concentration ratio, or to prepare multiple samples with different dilution ratios or concentration ratios and perform multiple assays to find the concentration of the target component.

The problem to be solved by this invention is to provide a chromatographic data processing device, data processing method, and chromatographic analysis system able to perform chromatographic analysis without relying on the experience or intuition of the assayer by adjusting the concentration of the target component in the sample to the appropriate value.

Means for Solving the Problem

The chromatographic data processing device in this invention is:

A data processing device that processes 3D data for time, analysis parameters, and signal strength obtained from 3D chromatography performed for a sample containing a target component, Characterized in that it is furnished with:

a) A setting means that sets analysis parameter P1 for the peak top of the peak of the target component in a spectrum that traverses said peak top, and analysis parameter P2 separate from the aforesaid analysis parameter P1 belonging to said peak, based on the aforesaid 3D data, b) A calculation means that calculates the ratio of the signal strength of the aforesaid analysis parameter P1 to the signal strength of the aforesaid analysis parameter P2 for the spectrum at each time under the aforesaid peak, c) A correction value setting means that sets the correction value based on the ratio of signal strength at each time calculated by the aforesaid calculation means, and d) A coefficient determining means that finds the estimated value for the peak strength of the aforesaid target component in a chromatogram at the aforesaid peak top analysis parameter P1 based on the aforesaid correction value and peak strength of the aforesaid target component in a chromatogram at the aforesaid analysis parameter P2, and determines the concentration adjustment coefficient such that the value thereof, when multiplied by said estimated value, falls within the range from a designated lower strength value limit to upper strength value limit for the aforesaid 3D chromatography.

Here, "analysis parameter" signifies wavelength, m/z (mass-to-charge ratio), or the like. Furthermore, range from a designated lower strength value limit to upper strength value limit indicates so-called dynamic range, determined based on signal processing limitations and the assay accuracy limitations of the detector used for 3D chromatographic analysis.

Another form of the chromatographic data processing device in this invention is:

A data processing device that processes 3D data for time, analysis parameters, and signal strength obtained from 3D chromatography performed for a sample containing a target component, Characterized in that it is furnished with:

a) A setting means that sets analysis parameter P1 for the peak top of the peak of the target component in a spectrum that traverses said peak top, and analysis parameter P2 separate from the aforesaid analysis parameter P1 belonging to said peak, based on the aforesaid 3D data, b) A calculation means that calculates the ratio of the signal strength of the aforesaid analysis parameter P1 to the signal strength of the aforesaid analysis parameter P2 for the spectrum at each time under the aforesaid peak, c) Plotting means that shows the relationship between the aforesaid signal strength ratio and the time of the spectrums for which said signal strength ratio was found, d) Correction value selection means that permits the user to select one value from among the aforesaid plotted signal strength ratios as the correction value, and e) A coefficient determining means that finds the estimated value for the peak strength of the aforesaid target component in a chromatogram at the aforesaid peak top analysis parameter P1 based on the aforesaid correction value and peak strength of the aforesaid target component in a chromatogram at the aforesaid analysis parameter P2, and determines the concentration adjustment coefficient such that the value thereof, when multiplied by said estimated value, falls within the range from a designated lower strength value limit to upper strength value limit for the aforesaid 3D chromatography.

The chromatographic data processing method in this invention is:

A chromatographic data processing method that processes 3D data for time, analysis parameters, and signal strength obtained from 3D chromatography performed for a sample containing a target component, Characterized in that it:

a) Sets analysis parameter P1 for the peak top of the peak of the target component in a spectrum that traverses said peak top, and analysis parameter P2 separate from the aforesaid analysis parameter P1 belonging to said peak, based on the aforesaid 3D data, b) Calculates the ratio of the signal strength of the aforesaid analysis parameter P1 to the signal strength of the aforesaid analysis parameter P2 for the spectrum at each time under the aforesaid peak, c) Sets the correction value based on the aforesaid calculated ratio of each time's signal strength, d) Finds an estimated value for the peak strength of the aforesaid target component in a chromatogram at the aforesaid analysis parameter P1 based on the aforesaid correction value and the peak strength of the aforesaid target component in a chromatogram at the aforesaid analysis parameter P2, and e) Determines the concentration adjustment coefficient such that the value thereof, when multiplied by said estimated value, falls within the range from a designated lower strength value limit to upper strength value limit for the aforesaid 3D chromatography.

Another form of the chromatographic data processing method in this invention is:

A chromatographic data processing method that processes 3D data for time, analysis parameters, and signal strength obtained from 3D chromatography performed for a sample containing a target component, Characterized in that it:

a) Sets analysis parameter P1 for the peak top of the peak of the target component in a spectrum that traverses said peak top, and analysis parameter P2 separate from the aforesaid analysis parameter P1 belonging to said peak, based on the aforesaid 3D data, b) Calculates the ratio of the signal strength of the aforesaid analysis parameter P1 to the signal strength of the aforesaid analysis parameter P2 for the spectrum at each time under the aforesaid peak, c) Displays the relationship between the aforesaid signal strength ratio and the time of the spectrums for which said signal strength ratio was found on a viewing screen, d) Permits the user to select one value from among the signal strength ratios displayed on the aforesaid viewing screen as the correction value, e) Finds the estimated value for the peak strength of the aforesaid target component in a chromatogram at the aforesaid analysis parameter P1 based on the aforesaid correction value and on the peak strength of the aforesaid target component in a chromatogram at the aforesaid analysis parameter P2, and f) Determines the concentration adjustment coefficient such that the value thereof, when multiplied by said estimated value, falls within the range from a designated lower strength value limit to upper strength value limit for the aforesaid 3D chromatography.

The spectrum of a given component has a shape unique to that component that does not differ depending on the concentration thereof. This uniformity of spectrum shape means that the signal strength of each analysis parameter for the chromatogram peak under the same peak will have a mutually invariable relationship. Accordingly, this relationship means that the chromatogram peak strength for a separate analysis parameter P2 belonging to the same peak can be used to estimate the chromatogram peak strength for peak top analysis parameter P1. In this case, if for some reason the strength of analysis parameter P1 or the strength of analysis parameter P2 should contain significant errors, for example because the signal strength of peak top analysis parameter P1 or the signal strength of analysis parameter P2 is beyond the dynamic range, the shape of the spectrum for that time will not be correct, so the relationship between both of these signal strengths, as calculated for this time, will also fall outside of the aforesaid invariable relationship. This is why a designated reference point is provided ahead of time, and a relationship within a time span with little error is used.

For example, if the analysis parameter is frequency, in this invention, first, a peak top wavelength $\lambda 1$ and wavelength $\lambda 2$ separate from the aforesaid wavelength $\lambda 1$ under the peak of the target component are set for the spectrum that traverses the peak top of the peak of the target component in the 3D data. The strength of this wavelength $\lambda 2$ is deemed to fall within the bounds of the dynamic range. Moreover, solely in instances where the peak top strength of the peak of the target component exceeds the upper limit value of the dynamic range, if the peak top strength does not exceed said upper limit value after setting the aforesaid wavelength $\lambda 1$ and wavelength $\lambda 2$ and calculating a correction value in the manner described below, it is acceptable to calculate an assay value for the target component by the conventional method from the chromatogram peak of peak top wavelength $\lambda 1$.

Next, the ratio of the strength at peak top wavelength $\lambda 1$ to the strength at wavelength $\lambda 2$ is calculated for the spectrum at each time under the peak of the target component. Next, the value of the strength ratio for the time span with the smallest error in strength at wavelength $\lambda 1$ and/or strength at wavelength $\lambda 2$ is then selected as the correction value by means of a designated selection criteria. The aforesaid peak strength at wavelength $\lambda 1$ of the chromatogram can then be estimated by using the correction value and the peak strength of the target component at wavelength $\lambda 2$ of the chromatogram. Next, a concentration adjustment coefficient is found that when multiplied by the estimated value for the aforesaid peak strength at wavelength $\lambda 1$ of the chromatogram will produce a value that falls within the dynamic range. This concentration adjustment coefficient reflects the concentration of the target component in the sample used when obtaining the aforesaid 3D chromatogram. In short, if a sample has a concentration adjustment coefficient of 1, that sample contains the target component in a suitable concentration range. For this reason, the peak strength of the target component on a 3D chromatogram obtained by 3D chromatography performed with said sample will fall within the dynamic range.

In contrast, if a sample has a concentration adjustment coefficient greater than 1, this means that the concentration of the target component in said sample is below the optimal concentration for chromatographic analysis, while if a sample has a concentration adjustment coefficient smaller than 1, this means that the concentration of the target component in said sample exceeds the optimal concentration for chromatographic analysis. Accordingly, in such cases, preprocessing would be performed by concentrating or diluting the sample by a factor corresponding to the concentration adjustment coefficient. Doing so makes it possible to accurately find the assay value for the target component by ensuring that the peak strength of the target component in a 3D chromatogram obtained for the preprocessed sample neither exceeds the upper limit value nor falls below the lower limit value for dynamic range.

In this case, the entire process from setting the sample to calculating an assay value for the target component in the sample can be automated by rendering it possible for a chromatography instrument to automatically perform both preprocessing involving concentrating/diluting the sample based on a concentration adjustment coefficient found by the chromatographic data processing device as well as 3D chromatographic analysis of the preprocessed sample.

In short, the chromatographic analysis system in this invention is:

A system furnished with a chromatography instrument furnished with a sample insertion device for inserting a sample into a column and a chromatographic data processing device that processes 3D data for time, analysis parameters, and signal strength obtained from 3D chromatography performed by said chromatography instrument, Characterized in that the aforesaid chromatographic data processing device is furnished with:

a) A setting means that sets analysis parameter P1 for the peak top of the peak of the target component in a spectrum that traverses said peak top, and analysis parameter P2 separate from the aforesaid analysis parameter P1 belonging to said peak, based on the aforesaid 3D data, b) A calculation means that calculates the ratio of the signal strength of the aforesaid analysis parameter P1 to the signal strength of the aforesaid analysis parameter P2 for the spectrum at each time under the aforesaid peak, c) Correction value setting means that sets the correction value based on the ratio of signal strength at each time calculated by the aforesaid calculation means, d) A coefficient determining means that finds the estimated value for the peak strength of the aforesaid target component in a chromatogram at the aforesaid peak top analysis parameter P1 based on the aforesaid correction value and peak strength of the aforesaid target component in a chromatogram at the aforesaid analysis parameter P2, and determines the concentration adjustment coefficient such that the value thereof, when multiplied by said estimated value, falls within the range from a designated lower strength value limit to upper strength value limit for the aforesaid 3D chromatography, and e) Output means that outputs the aforesaid concentration adjustment coefficient, and The aforesaid liquid chromatographic analysis device is furnished with:

f) A preprocessing portion that performs preprocessing of the aforesaid sample based on a concentration adjustment coefficient output from the aforesaid chromatographic data processing device, and a chromatographic analysis performance portion that performs 3D chromatography for the preprocessed sample.

Effect of the Invention

According to this invention, in the event that the signal strength obtained by performing 3D chromatography for a sample containing a target component falls outside of the dynamic range of said 3D chromatography, a concentration adjustment coefficient that serves as an index for indicating the extent by which it falls outside of the dynamic range can be automatically found, which makes it possible to perform 3D chromatographic analysis on a sample that has been appropriately preprocessed by dilution/concentration or the like without having to rely on the experience or intuition of an assayer.

DETAILED DESCRIPTION OF THE EXEMPLARY EMBODIMENTS

Below, a chromatographic analysis system comprising a liquid chromatography instrument and the data processing device thereof will be described by way of example as an embodiment example of this invention.

Figure 1:
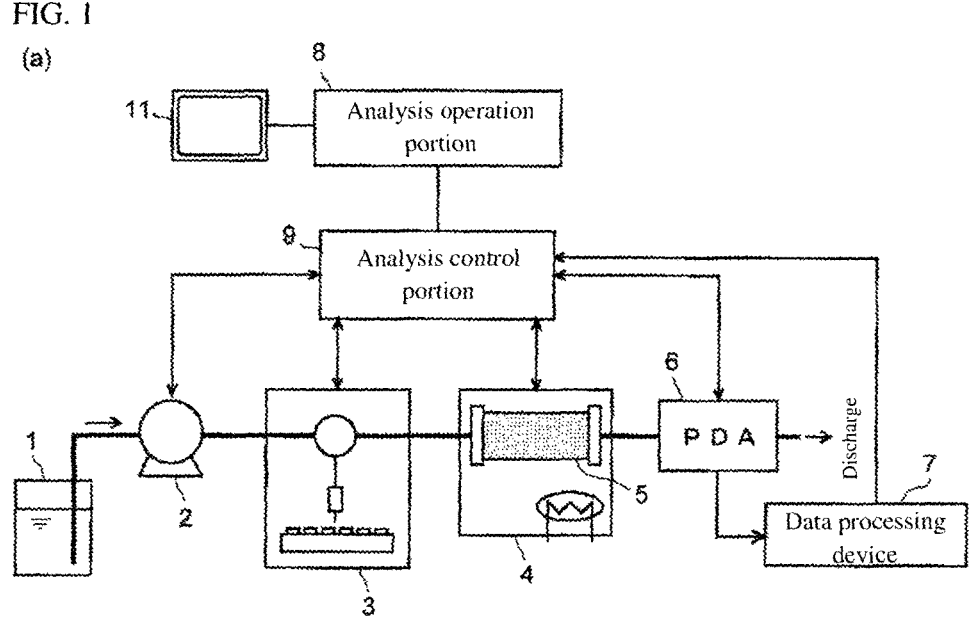
FIG. 1 is a schematic illustration of the configuration of an embodiment of the analysis system including a chromatographic data processing device in this invention.
Figure 1:
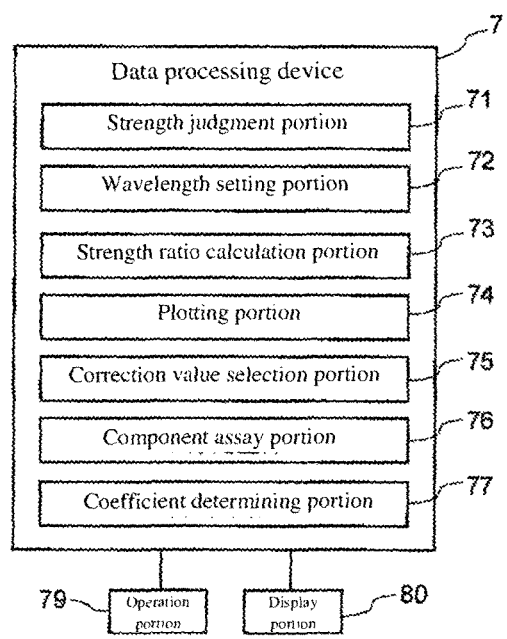

FIG. 1 at (a) is a schematic illustration of the configuration of the analysis system equipped with a chromatographic data processing device in this embodiment example. This analysis system is furnished with a pump 2 that supplies the mobile phase at a constant flow from a mobile phase vessel 1 by suction, autosampler 3 that selects and collects samples from multiple liquid samples prepared on a rack in a designated sequence, and then performs the necessary preprocessing such as dilution, concentration, etc. before injecting the sample into the mobile phase supplied by the aforesaid pump 2, column oven 4 having a column 5 on the interior thereof into which the liquid sample is sent by the mobile phase that controls the temperature of said column 5, photodiode array detector (PDA) 6 that detects the spectrum for each component within the designated frequency range, and data processing device 7 that processes data output from the PDA 6. The pump 2, autosampler 3, column oven 4, and PDA 6 are controlled by an analysis control portion 9 based on instructions from an analysis operation portion 8. The pump 2, autosampler 3, column oven 4, column 5, PDA 6, analysis operation portion 8, analysis control portion 9, etc. together comprise the liquid chromatographic instrument in this invention.

Practically speaking, the data processing device 7 will be a standard computer comprising a CPU (central processing unit), memory, and storage device such as hard disk or SSD. Dedicated data processing software is installed on this computer, and this software is run to implement the functions of the strength judgment portion 71, wavelength setting portion 72, strength ratio calculation portion 73, plotting portion 74, correction value selection portion 75, component assay portion 76, coefficient determining portion 77, etc. shown in FIG. 1 at (b). Furthermore, an operating portion 79 consisting of a keyboard and a pointing device such as a mouse or the like and a display portion 80 are connected to the data processing device 7.

Figure 2:
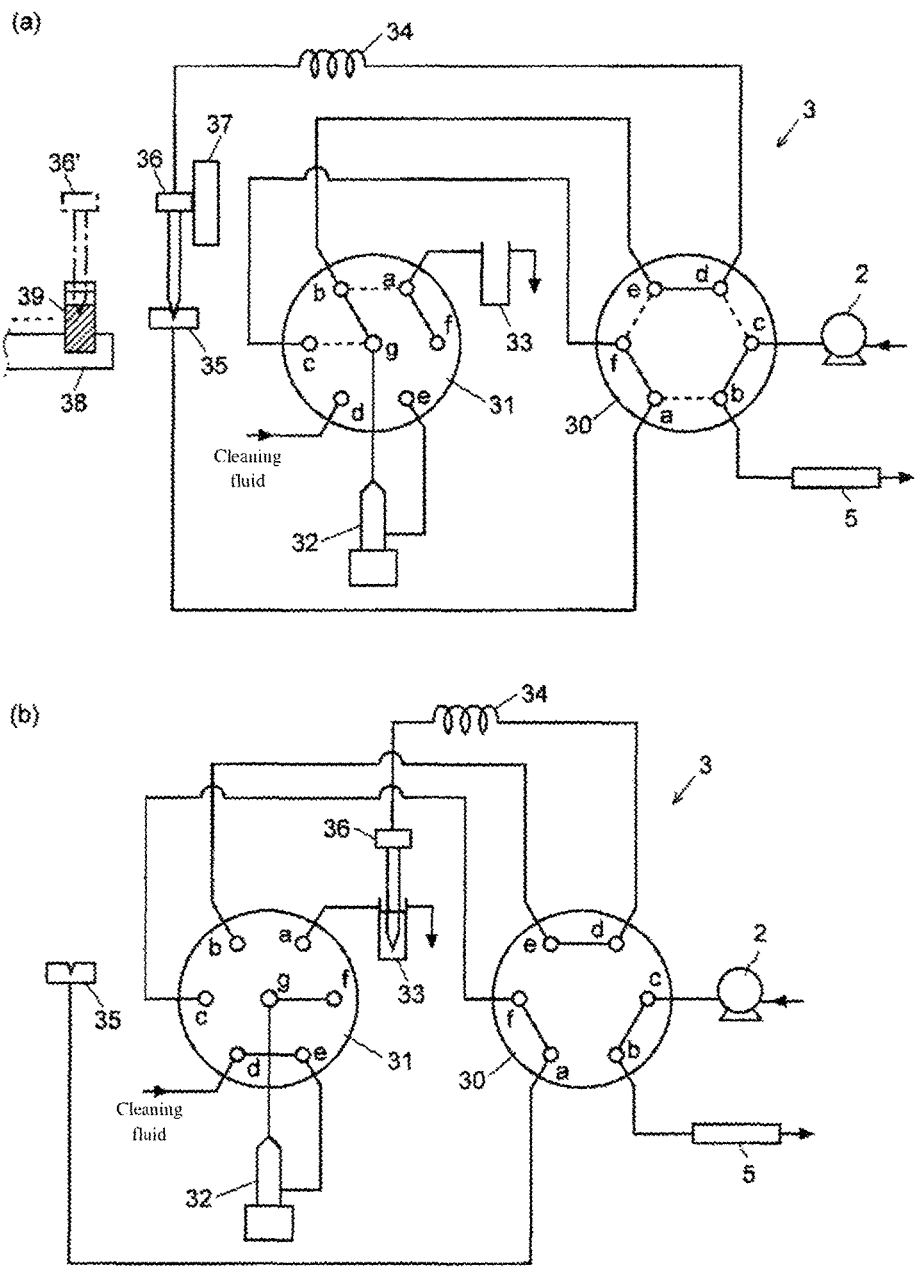
FIG. 2 is a schematic of the flow path serving to illustrate the operation of the autosampler comprising the analysis system in this embodiment example.

FIG. 2 shows an example configuration of the autosampler 3 and a schematic of the flow path serving to illustrate the operation thereof. In FIG. 2, the injection valve (high-pressure valve) 30 is a rotary 6-port 2-position flow path switching valve with 6 ports 30a-30f, which can be switched to selectively connect to two adjoining ports. In short, it is possible to switch between two connection combinations, respectively indicated by the solid and dotted lines in FIG. 2 at (a). In contrast, the low-pressure valve 31 is a rotary 7-port 6-position valve with seven ports 31a-31g. When common port 31g, which is connected to measurement pump 32, is coupled to one of the other six ports 31a-31f, this causes the two designated adjoining ports from among ports 31a-31a to become coupled. For example, when common port 31g is coupled to port 31b, as indicated by the solid line in FIG. 2 at (a), this causes ports 31a and 31f to become coupled.

The column flow path, which leads to the column 5, is connected to port 30b of the injection valve 30, and the mobile phase flow path, through which the pump 2 supplies the mobile phase, is connected to port 30c. One end of the sample loop 34 is connected to port 30d, and the other end is connected to port 30a across the needle 36 and the injection port 35. Port 30e and port 30f are connected to port 31b and port 31c of the low-pressure valve 31, respectively. The cleaning port 33 is connected to port 31a of this low-pressure valve 31, port 31e is connected to the measurement pump 32, and cleaning fluid is supplied to port 31d. The sample rack 38 houses multiple vials 39 that retain liquid samples, diluent, or the like. The needle 36 can be moved horizontally and vertically by a movement mechanism 37, such that it can be moved above the vial 39 and the cleaning port 33 and inserted into the liquid therein.

The basic operating sequence when introducing a sample into this autosampler 3 will be described. To collect a sample, the injection valve 30 and the low-pressure valve 31 are switched to the connection state indicated by the solid line in FIG. 2 at (a), and the needle 36 is moved above the vial 39 and inserted into the liquid sample therein (position at symbol 36'). In this position, when the plunger of the measurement pump 32 is pulled, a liquid sample is aspirated from the vial 39 through the mobile phase (or cleaning fluid made of the same component) that fills the flow path leading from the measurement pump 32 to the needle 36, and that liquid sample is retained in the sample loop 34. The amount of liquid sample collected is equivalent to the aspiration volume of the measurement pump 32.

After a sample has been collected, the needle 36 is returned to its position above the injection port 35 and connected to the injection port 35. Next, the injection valve 30 is switched to the connection state indicated by the dotted line in FIG. 2 at (a). This causes the mobile phase supplied by the pump 2 to be sent to the column 5 via the sample loop 34, needle 36, and injection port 35. At this time, the liquid sample that was previously retained in the sample loop 34 is sent into the column 5 together with the mobile phase.

The needle 36 is cleaned of liquid sample adhered thereto by this sample aspiration as follows. Namely, the injection valve 30 and the low-pressure valve 31 are switched to the connection state indicated by the solid line in FIG. 2 (b). This causes the plunger of the measurement pump 32 to be pulled, drawing cleaning fluid into the syringe. Next, the injection valve 30 and the low-pressure valve 31 are both switched to the connection state indicated by the dotted line in FIG. 2 at (a), causing the plunger to be pushed, discharging cleaning fluid from the measurement pump 32, causing cleaning fluid to be guided into and fill the cleaning port 33, with any excess cleaning fluid discharged from the drainage port of the cleaning port 33. Next, as shown in FIG. 2 (b), the needle 36 is moved above the cleaning port 33 and immersed in the cleaning fluid retained in the cleaning port 33, where the needle 36 is cleaned for a fixed length of time before being returned to the injection port 35.

The above operations are only the most basic operations, and the sequence of operations will be rendered more complicated by the addition of preprocessing such as concentration or dilution of the target component in the sample, addition of reagent, etc. However, either way, the operations of each mechanism system, i.e. valves 30, 31, measurement pump 32, movement mechanism 37, etc., will be performed in sequence when the autosampler 3 carries out a sequence of operations.

Figure 3:
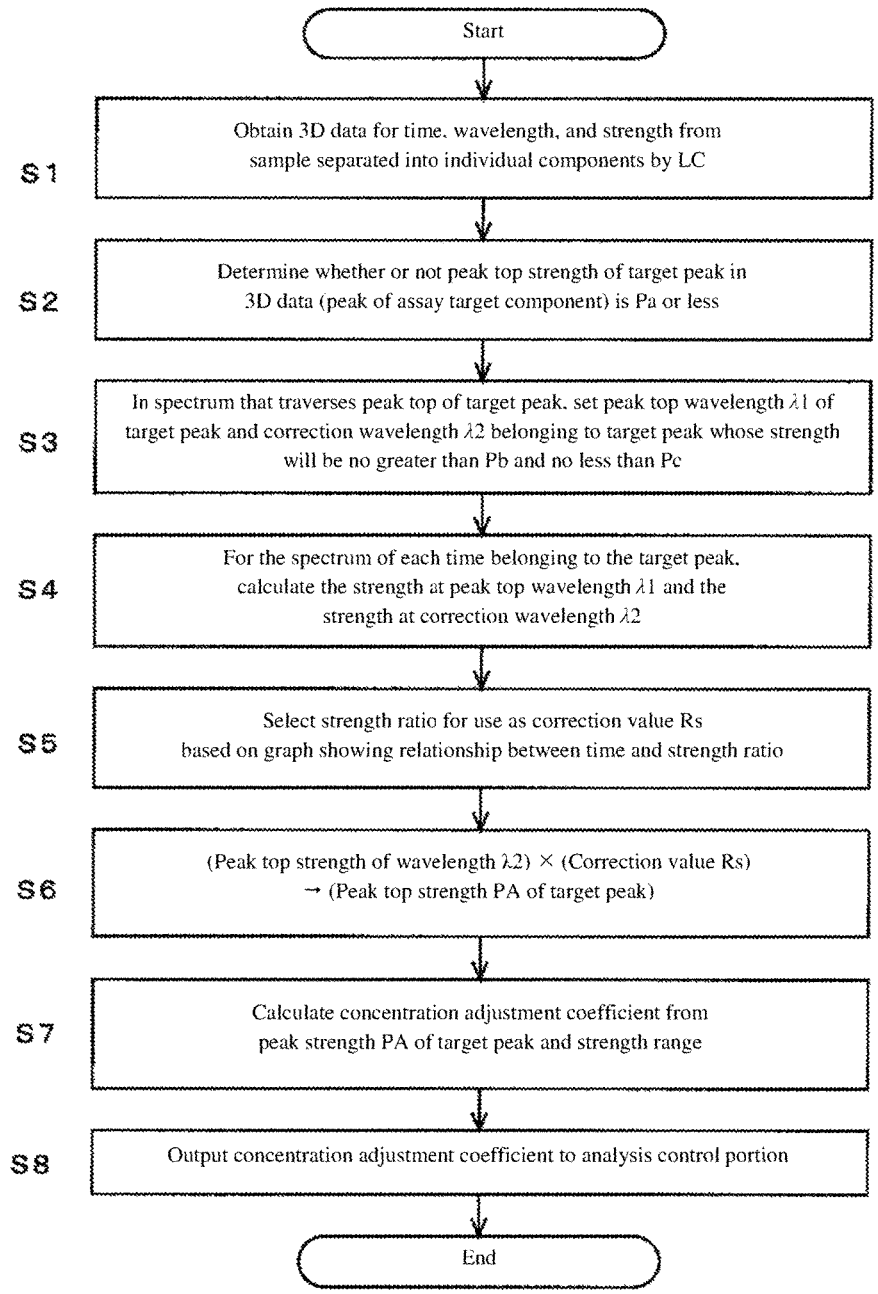
FIG. 3 is a brief flowchart of data processing in the chromatographic data processing device in this embodiment example.

Next, the operation of determining the concentration adjustment coefficient for the liquid sample, which is a characteristic operation of the chromatographic analysis system in this embodiment example, will be described with reference to the flowchart in FIG. 3.

Prior to determining the concentration adjustment coefficient, chromatographic analysis is conducted on a liquid sample in a designated vial 39 set in a sample rack 38 of a liquid chromatogra[phy] instrument. In short, the autosampler 3 collects a designated amount of liquid sample from a designated vial 39 in the sample rack 38, and introduces it into the column 5 of the liquid chromatography instrument. The operations from collecting the liquid sample to introducing said liquid sample into the column 5 are as described above. Moreover, at this time, preprocessing such as concentrating or diluting the liquid sample is not performed.

Figure 4:
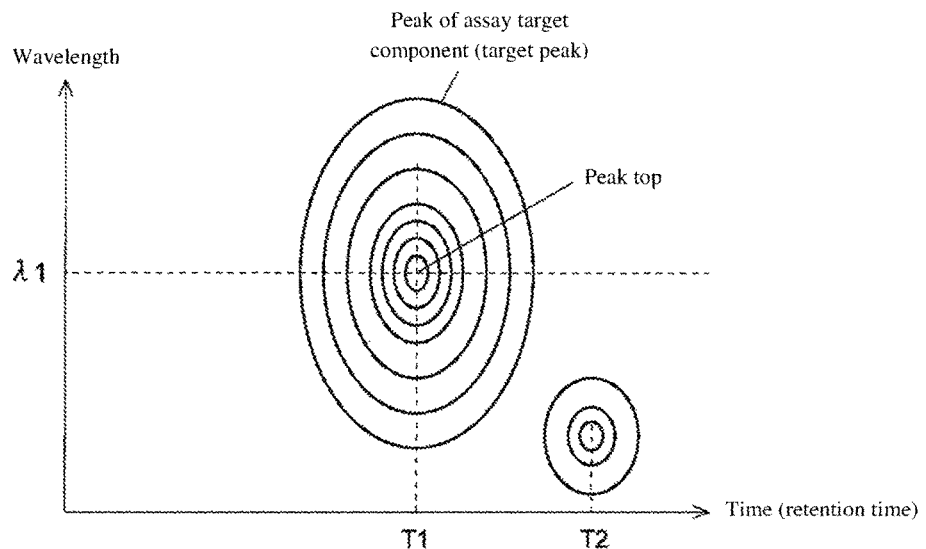
FIG. 4 is a contour map showing 3D data obtained by the chromatographic data processing device in this embodiment example.

When the liquid sample is introduced into the column 5, each component contained in said liquid sample is chronologically separated, and a spectrum of a designated frequency range is detected for each component by the PDA 6. This detection data (spectrum data) is successively sent to the data processing device 7, and as a result, 3D data for time, frequency, and strength of the kind shown in FIG. 4 are obtained. (Step S1) The strength judgment portion 71 of the data processing device 7 determines whether or not the peak top strength of the peak of the target component in this 3D data (hereinafter the "target peak") exceeds a designated upper limit value Pa. (Step S2) This upper limit value Pa is a value that has been pre-set in the data processing device 7 according to the dynamic range of the PDA 6, A/D converter (not shown), etc. Typically, the upper limit value of the dynamic range is used, but a safer value lower than this may be used instead, or a practically tolerable value slightly higher than this may be used instead.

In Step S2, if the peak top strength of the target peak does not exceed the upper limit value Pa, the component assay portion 76 of the data processing device 7 calculates the assay value of the target component (peak surface area or peak height) by the conventional method from a chromatogram along the peak top wavelength $\lambda 1$ of the target peak.

In contrast, in the event that the peak top strength of the target peak should exceed the upper limit value Pa, then even if the assay value of the target component were to be calculated from a chromatogram along the peak top wavelength $\lambda 1$ of the target peak, it would not be an accurate value. For this reason, the concentration adjustment coefficient of the liquid sample is determined by the following process.

Figure 5:
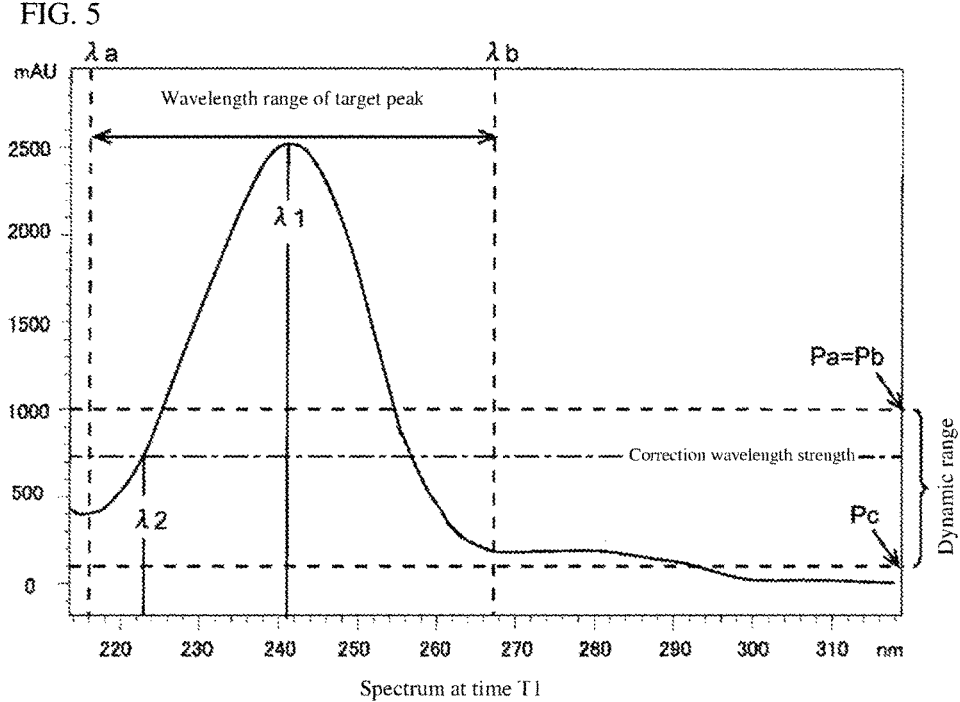
FIG. 5 shows a spectrum along time T1 obtained from the aforesaid 3D data.

In Step S3, the wavelength setting portion 72 sets a peak top wavelength $\lambda 1$ and a wavelength whose strength is no greater than a designated upper limit value Pb and no less than a designated lower limit value Pc (hereinafter the "correction wavelength") $\lambda 2$ within the wavelength range belonging to the target peak in a spectrum that traverses the peak top of the target peak (the spectrum along time T1 in FIG. 4). (FIG. 5) This upper limit value Pb, like the aforesaid upper limit value Pa, is a value that has been pre-set in the data processing device 7 according to the upper limit value of the dynamic range of the PDA 6, etc. The upper limit value Pa used in Step S3 and the upper limit value Pb used in Step S4 may be the same, or they may be different. In this embodiment example, Pa=Pb.

Furthermore, the lower limit value Pc is a value set in advance in the data processing device 7 according to the lower limit value of the dynamic range, and although typically set to the lower limit value of the dynamic range, may instead be set to a value slightly higher than this.

Figure 6:
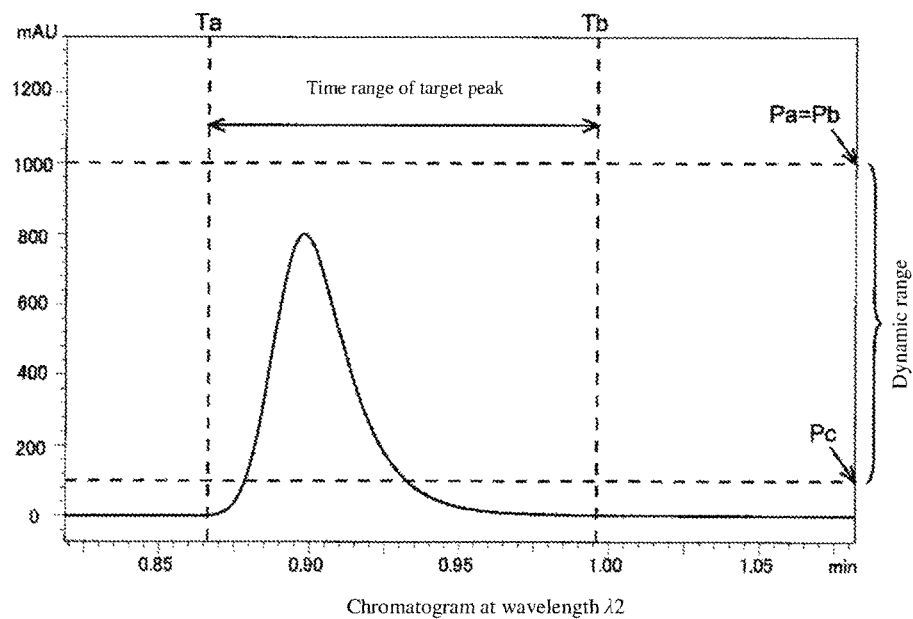
FIG. 6 shows a chromatogram along corrective wavelength λ2 obtained from the aforesaid 3D data.
Figure 7:
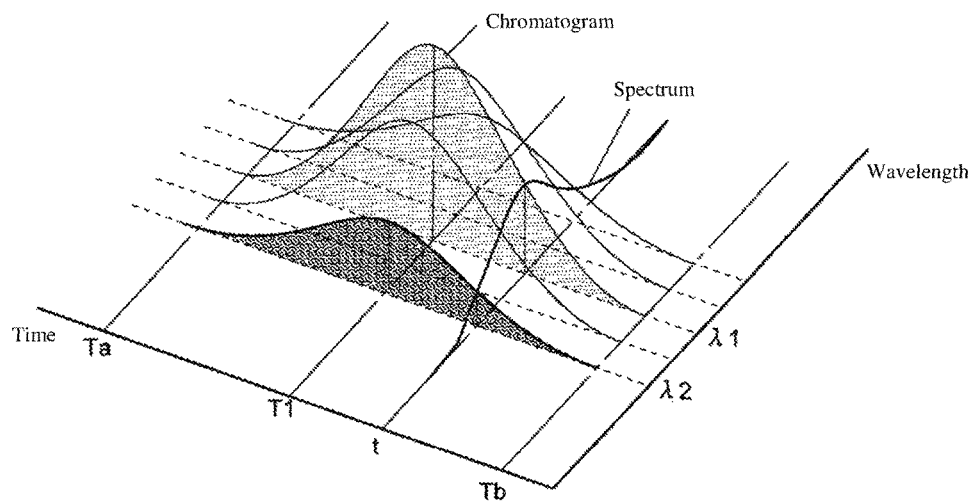
FIG. 7 is a 3D graph of time, wavelength, and strength indicating the processing principle when calculating the strength ratio.
Figure 8:
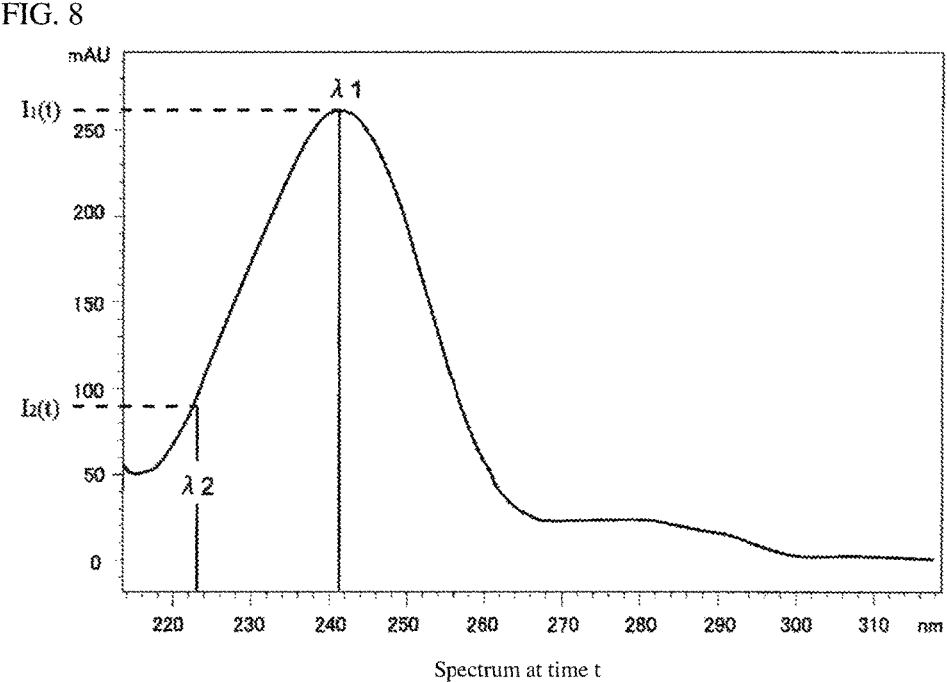
FIG. 8 shows a spectrum at a given time t belonging to the target peak.

The strength ratio calculation portion 73 produces a chromatogram at correction wavelength $\lambda 2$ from the aforesaid 3D data (correction chromatogram). (FIG. 6) Next, for each time t within the time span (Ta, Tb) under the target peak (FIG. 6 and FIG. 7) on this correction chromatogram, the strength $I_1(t)$ of wavelength $\lambda 1$ and the strength $I_2(t)$ of correction wavelength $\lambda 2$ are obtained (FIG. 8), and the strength ratio R(t) is calculated from the ratio thereof by the following formula. (Step S4) (strength ratio R(t))=(strength $I_1(t)$ at wavelength $\lambda 1$)/(strength $I_2(t)$ at correction wavelength $\lambda 2$)

Figure 9:
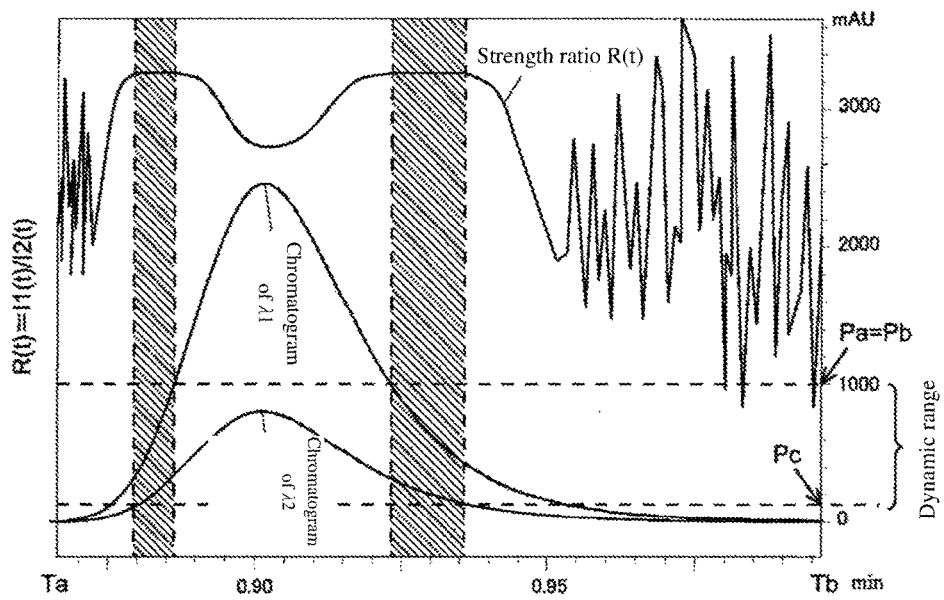
FIG. 9 is a graph indicating relationship between time and strength ratio, and chromatogram at peak top wavelength λ1 and corrective wavelength λ2.
Figure 10:
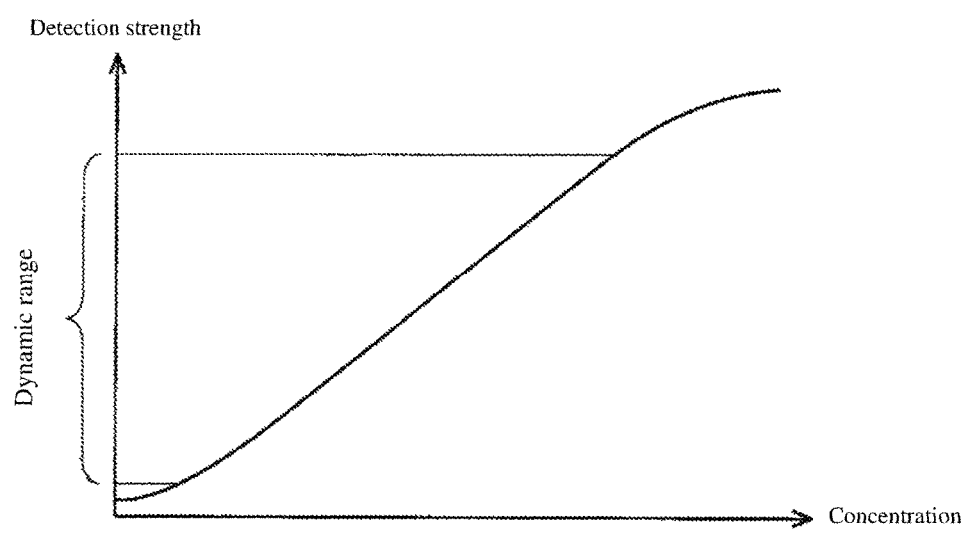
FIG. 10 is a diagram illustrating the dynamic range of the detector.

The plotting portion 74 creates a graph of this strength ratio R(t) and displays it on the display portion 80. Strength ratio R(t), as shown in FIG. 9, falls outside of a uniform value, creating dissimilarity in the spectrum shapes, when at least one of either strength $I_1(t)$ or strength $I_2(t)$ fall outside of the scope of the dynamic range. In contrast, when both strength $I_1(t)$ and strength $I_2(t)$ fall within the scope of the dynamic range, the strength ratio R(t) attains a roughly uniform value. For this reason, the greatest similarity in spectrum shape is maintained when both strength $I_1(t)$ and strength $I_2(t)$ fall within the scope of the dynamic range, providing the greatest reliability. In this embodiment example, the correction value selection portion 75 automatically sets the correction value Rs to the median of the strength ratio R(t) when strength $I_1(t)$ and strength $I_2(t)$ fall within the scope of the dynamic range. (Step S5)

The coefficient determining portion 77 uses the correction value Rs set in this way to calculate the peak top strength PA of the chromatogram along the peak top wavelength $\lambda 1$ of the target peak to a value obtained by multiplying the peak top strength of the chromatogram of the correction wavelength $\lambda 2$ by the correction value Rs. (Step S6)

The concentration adjustment coefficient 1/D is then calculated so that, when this value is multiplied by the peak top strength PA of the target peak, this will produce a value that falls between the lower limit value Pc and the upper limit value Pa of the dynamic range. (Step S7) In this embodiment example, to ensure that the peak top strength of the target peak falls within the dynamic range, said concentration adjustment coefficient 1/D is calculated in such a way that the value obtained by multiplying the aforesaid peak top strength PA by the concentration adjustment coefficient 1/D falls within the correction strength range of no less than 3 times the lower limit value Pc and no greater than ½ the upper limit value Pa. Moreover, "D" in the concentration adjustment coefficient 1/D corresponds to the dilution ratio. In this embodiment example, in order to facilitate preprocessing such as dilution/concentration of the liquid sample, D is an integer, and an integer D is found such that the value obtained by multiplying the peak top strength PA by 1/D (PA×(1/D)) attains the largest possible value within the aforesaid correction strength range.

For example, if the dynamic range is 0.4 mAU to 2000 mAU, and the peak top strength PA of the target peak calculated in Step S6 is 5633 mAU, the integer D where PA×(1/D) produces the largest possible value within the strength range of 1.2 mAU to 1000 mAU is "6." Accordingly, the coefficient determining portion 77 selects "⅙" as the concentration adjustment coefficient.

The concentration adjustment coefficient 1/D found in Step S7 is output from the data processing device 7 to the analysis control portion 9. (Step S8) The analysis control portion 9 instructs the autosampler 3 to carry out preprocessing in accordance with the value of the concentration adjustment coefficient 1/D. Specifically, the autosampler 3 is controlled in such a way as to carry out the preprocessing of diluting the liquid sample with diluent by D times, and then introduce it into the column 5. Next, the processing in the above-described Steps S2 to S3 is carried out, but because the peak top strength PA of the target peak now falls within the range of the lower limit value Pc to the upper limit value Pa (the dynamic range) as a result of having carried out the process of diluting the liquid sample, the assay value for the target component in the liquid sample is calculated by the conventional method.

When the assay value for the target component has been calculated, the data processing device 7 divides said assay value by the concentration adjustment coefficient 1/D. This produces the assay value for the target component in the liquid sample.

Moreover, although in the above-described embodiment example the liquid sample was diluted at dilution ratio D after finding the concentration adjustment coefficient 1/D and then introduced into the column 5, the amount of the liquid sample introduced into the column 5 may alternately be changed to 1/D.

Furthermore, although in the above-described embodiment example a case was described in which the peak top strength of the liquid sample exceeded the upper limit value of the dynamic range, this invention may equally well be applied in cases where the peak top strength of the liquid sample falls below the lower limit value of the dynamic range. In this case, the concentration adjustment coefficient 1/D will attain a value larger than 1 (in other words, D will attain a value smaller than 1), so the liquid sample can either be concentrated at concentration ratio D as preprocessing prior to chromatographic analysis, or the quantity of the liquid sample introduced into the column can be increased by 1/D-fold. Doing this will cause the peak strength of the target component obtained from chromatographic analysis to fall within the dynamic range, making it possible to accurately find the assay value for the target component in the liquid sample.

Moreover, rather than having the correction value selection portion 75 automatically set the correction value Rs, it is also acceptable for the user to be made to select one strength ratio from the graph of strength ratios R(t) displayed on the display portion 80.

Alternately, correction wavelength λ2 can be automatically determined by the wavelength setting portion 72 based on the 3D data. The following are methods of automatically setting correction wavelength λ2.

Obtain the spectrum at retention time T1 of the target peak.

For this spectrum, use the wavelength at which the strength value on the + side (long-wavelength side) or − side (short wavelength side) of the peak top wavelength λ1 attains the "correction wavelength strength" set in advance by the user as the correction wavelength λ2. (FIG. 5) The + or − search direction can be specified by the user in advance, or can be determined by the system. (In FIG. 5, searching is towards the − side)

Furthermore, although in the embodiment example described above a determination was made as to whether or not the peak top strength of the target component peak exceeds the upper limit value Pa, and the processing in Steps S3 to S7 was performed only if so, this processing may alternately be performed at all times.

DESCRIPTION OF REFERENCES

1: Mobile phase bottle
2: Pump
3: Autosampler
4: Column oven
5: Column
6: Detector (PDA)
7: Data processing device
71: Strength judgment portion
72: Wavelength setting portion
73: Strength ratio calculation portion
74: Plotting portion
75: Correction value selection portion
76: Component assay portion
77: Coefficient determining portion
8: Analysis operation portion
9: Analysis control portion
30: Injection valve
31: Low-pressure valve
32: Measurement pump
33: Cleaning port
34: Sample loop
36: Needle
37: Movement mechanism
38: Sample rack
39: Vial

What is claimed:

1. A chromatograph analysis system comprising:
   a chromatography instrument that performs 3D chromatography on a sample containing a target component to obtain 3D data for time, an analysis parameter, and a signal strength; and
   a chromatographic data processing device comprising a processor configured to, based on receiving the 3D data for the time, the analysis parameter and the signal strength from the chromatography instrument:
   a) set a peak top analysis parameter P1 for a peak top of a peak of the target component in a spectrum that traverses the peak top, and an analysis parameter P2 separate from the peak top analysis parameter P1, based on the 3D data,
   b) calculate a ratio of the signal strength of the peak top analysis parameter P1 to the signal strength of the analysis parameter P2 for the spectrum at each of a plurality of time points within a time span under the peak,
   c) set a correction value based on the calculated ratio of the signal strength at each of the plurality of time points within the time span,
   d) determine an estimated value for the peak strength of the target component in a chromatogram at the peak top analysis parameter P1 based on the correction value and the peak strength of the target component in a chromatogram at the analysis parameter P2,
   e) determine a concentration adjustment coefficient such that the value thereof, when multiplied by the estimated value, falls within a range from a designated lower strength value limit to an upper strength value limit for the 3D chromatography, and
   f) adjust a concentration of the target component in the sample to an appropriate value based on the determined concentration adjustment coefficient.

2. The chromatographic analysis system set forth in claim 1, wherein the processor is further configured to:
   judge whether or not the peak top strength of the peak of the target component exceeds a designated upper limit value, and
   in the event that the peak top strength exceeds the upper limit value, set the peak top analysis parameter P1 and an analysis parameter whose strength is no greater than the designated upper strength value limit and no less than the designated lower strength value limit as the analysis parameter P2.

3. The chromatographic analysis system as set forth in claim 1, wherein the processor is further configured to:
   g) perform 3D chromatography for the adjusted sample.

4. The chromatographic analysis system set forth in claim 1, wherein the processor is further configured to: automatically set the correction value to a median of the ratio of the signal strength when the strength of the peak top analysis parameter P1 and the strength of the analysis parameter P2 fall within the scope of the dynamic range.

5. The chromatographic analysis system set forth in claim 1, wherein the designated lower strength value limit and the upper strength value limit for the 3D chromatography are set in advance.

6. The chromatographic analysis system set forth in claim 1, wherein the analysis parameter signifies at least one of wavelength, m/z (mass-to-charge) ratio or frequency.

7. The chromatographic analysis system set forth in claim 1, wherein the analysis parameter is wavelength.

8. A chromatograph analysis system comprising:
a chromatography instrument that performs 3D chromatography on a sample containing a target component to obtain 3D data for time, an analysis parameter, and a signal strength; and
a chromatographic data processing device comprising a processor configured to, based on receiving the 3D data for the time, the analysis parameter, and the signal strength from the chromatography instrument:
   a) set a peak top analysis parameter P1 for a peak top of a peak of the target component in a spectrum that traverses the peak top, and an analysis parameter P2 separate from the peak top analysis parameter P1, based on the 3D data,
   b) calculate a ratio of the signal strength of the peak top analysis parameter P1 to the signal strength of the analysis parameter P2 for the spectrum at each of a plurality of time points within a time span under the peak,
   c) plot a relationship between the signal strength ratio and the time points of the spectrums for which the signal strength ratio was found,
   d) permit a user to select one value from among the plotted signal strength ratios as a correction value,
   e) determine an estimated value for the peak strength of the target component in a chromatogram at the peak top analysis parameter P1 based on the correction value and the peak strength of the target component in a chromatogram at the analysis parameter P2,
   f) determine a concentration adjustment coefficient such that the value thereof, when multiplied by the estimated value, falls within a range from a designated lower strength value limit to an upper strength value limit for the 3D chromatography, and
   g) adjust a concentration of the target component in the sample to an appropriate value based on the determined concentration adjustment coefficient.

9. The chromatographic analysis system set forth in claim 8, wherein the processor is further configured to:
judge whether or not the peak top strength of the peak of the target component exceeds a designated upper limit value, and
in the event that the peak top strength exceeds the upper limit value, set the peak top analysis parameter P1 and an analysis parameter whose strength is no greater than the designated upper strength value limit and no less than the designated lower strength value limit as the analysis parameter P2.

10. The chromatographic analysis system as set forth in claim 8, further comprising
   h) perform 3D chromatography for the adjusted sample.

11. A chromatographic data processing method comprising:
based on receiving 3D data for time, an analysis parameter, and a signal strength obtained from 3D chromatography performed for a sample containing a target component:
   a) setting a peak top analysis parameter P1 for a peak top of a peak of the target component in a spectrum that traverses the peak top and an analysis parameter P2 separate from the analysis parameter P1, based on the 3D data,
   b) calculating a ratio of the signal strength of the peak top analysis parameter P1 to the signal strength of the analysis parameter P2 for the spectrum at each of a plurality of time points within a time span under the peak,
   c) setting the correction value based on the calculated signal strength ratio at each of the plurality of time points within the time span,
   d) determining an estimated value for the peak strength of the target component in a chromatogram at the analysis parameter P1 based on the correction value and on the peak strength of the target component in a chromatogram at the analysis parameter P2,
   e) determining a concentration adjustment coefficient such that the value thereof, when multiplied by the estimated value, falls within a range from a designated lower strength value limit to an upper strength value limit for the 3D chromatography, and
   f) adjusting a concentration of the target component in the sample to an appropriate value based on the determined concentration adjustment coefficient.

12. The chromatographic data processing method set forth in claim 11, further comprising:
judging whether or not the peak top strength of the peak of the target component exceeds a designated upper limit value, and,
in the event that the peak top strength exceeds the upper limit value, setting the peak top analysis parameter P1 and an analysis parameter whose strength is no greater than the designated upper strength value limit and no less than the designated lower strength value limit as the analysis parameter P2.

13. A chromatographic data processing method comprising:
based on receiving 3D data for time, an analysis parameter, and a signal strength obtained from 3D chromatography performed for a sample containing a target component:
   a) setting a peak top analysis parameter P1 for a peak top of a peak of the target component in a spectrum that traverses the peak top, and analysis parameter P2 separate from the analysis parameter P1, based on the 3D data,
   b) calculating a ratio of the signal strength of the peak top analysis parameter P1 to the signal strength of the analysis parameter P2 for the spectrum at each of a plurality of time points within a time span under the peak,
   c) displaying a relationship between the signal strength ratio and the time points of the spectrums for which the signal strength ratio was found on a display screen,
   d) permitting a user to select one value from among the signal strength ratios displayed on the viewing screen as a correction value,
   e) determining an estimated value for the peak strength of the target component in a chromatogram at the peak top analysis parameter P1 based on the correction value and on the peak strength of the target component in a chromatogram at the analysis parameter P2,
   f) determining the concentration adjustment coefficient such that the value thereof, when multiplied by the estimated value, falls within a range from a designated lower strength value limit to an upper strength value limit for the 3D chromatography, and
   g) adjusting a concentration of the target component in the sample to an appropriate value based on the determined concentration adjustment coefficient.

14. The chromatographic data processing method set forth in claim 13, further comprising:

judging whether or not the peak top strength of the peak of the target component exceeds a designated upper limit value, and in the event that the peak top strength exceeds the upper limit value, setting the peak top analysis parameter P1 and an analysis parameter whose strength is no greater than the designated upper strength value limit and no less than the designated lower strength value limit as the analysis parameter P2.

* * * * *